United States Patent
Baxter-Jones (10) Patent No.: US 6,419,646 B1
(45) Date of Patent: Jul. 16, 2002

(54) DEVICES AND METHODS FOR CERVIX MEASUREMENT

(75) Inventor: Rosalyn Baxter-Jones, San Diego, CA (US)

(73) Assignee: Cervilenz, Irvine, CA (US)

( * ) Notice: Subject to any disclaimer, the term of this patent is extended or adjusted under 35 U.S.C. 154(b) by 0 days.

(21) Appl. No.: 09/546,099

(22) Filed: Apr. 10, 2000

(51) Int. Cl.$^7$ .......................... A61B 5/103; A61B 5/117

(52) U.S. Cl. ..................................... 600/591

(58) Field of Search .................. 600/591, 587; 264/222; 128/DIG. 23, 897, 898

(56) References Cited

U.S. PATENT DOCUMENTS

| | | | |
|---|---|---|---|
| 3,630,190 A | 12/1971 | Baker | 128/2 |
| 3,706,397 A | 12/1972 | Hasson | 600/591 |
| 4,016,867 A | 4/1977 | King et al. | 128/2 |
| 4,224,951 A | 9/1980 | Hasson | 128/778 |
| 4,489,732 A | 12/1984 | Hasson | 128/778 |
| 4,685,474 A | 8/1987 | Kurz et al. | 128/778 |
| 5,658,295 A | 8/1997 | Krementsov | 606/119 |
| 5,980,804 A | * 11/1999 | Koch | 264/222 |
| 6,039,701 A | 3/2000 | Sliwa et al. | 600/588 |

OTHER PUBLICATIONS

Phillip G. Stubblefield, M.D., "Preterm Birth: Causes, Prevention, and Management, Cervical Incompetence", Chapter 6, pp. 98–111 (1984).

I. Brook et al., Ultrasonography in the Diagnosis of Cervical Incompetence in Pregnancy–A New Diagnostic Approach, British Journal of Obstetrics and Gynecology, Jun. 1981, vol. 88, pp. 640–643.

Anderson et al., "Prediction of risk for preterm delivery by ultrasonographic measurement of cervical length." Am. J. Obstet. Gynecol. 163(3):859–867 (1990).

Iams et al., "The length of the cervix and the risk of spontaneous premature delivery." N. Eng. J. Med. 334(9):567–72 (1996).

Health et al., "Cervical length at 23 weeks of gestation: prediction of spontaneous preterm delivery." Ultrasound Obstet. Gynecol. 12:312–317 (1998).

Sonek et al. "Preterm Birth, Causes, Prevention and Management" Second Edition, chapter 5, McGraw–Hill, Inc. pp. 137–160 (1993).

Brook et al., J. Obstet. Gynecol 88:640 (1981).

Michaels et al. "Ultrasound differentiation of the competent from the incompetent cervix: Prevention of preterm delivery." Am. J. Obstet Gynecol. 154(3):537–546 (1986).

Sarti et al. "Ultrasonic Visualization of a Dilated Cervix During Pregnancy." Radiology 130:417–420 (1979).

Vaalamo and Kivikoski, "The incompetent Cervix During Pregnancy Diagnosed by Ultrasound." Acta Obstet. Gynecol Scand 62:19–21 (1983).

Anderson et al., "Relationship between length of gestation and cervical dilatation, uterine contractility, and other factors during pregnancy." Am. J. Obst. & Gynec. 105(8):1207–1214 (1969).

(List continued on next page.)

*Primary Examiner*—Kevin Shaver
*Assistant Examiner*—Brian Szmal
(74) *Attorney, Agent, or Firm*—Lyon & Lyon LLP (57) ABSTRACT

The present invention provides devices having an elongated member, a stop slidably engaged with the member and preferably a measuring scale to determine dimensions of female reproductive organs. Preferably, the device is adapted to determine the length of the cervix in the fornix vaginae, which is used in the disclosed methods to predict the risk of preterm labor, risk of miscarriage, ease or difficulty of inducing labor, and fertility of an individual. Additional embodiments of the device determine dimensions of the fornix vaginae and dilation of the cervix uteri.

17 Claims, 4 Drawing Sheets

OTHER PUBLICATIONS

Phillip G. Stubblefield, "Preterm Birth, Causes, Prevention, and Management." Second Edition, Chapter 1, McGraw–Hill, Inc. (1993).

Wood et al., "The prediction of premature labor by observation of the cervix and external tocography." Am. J. Obst. & Gynec. 91(3):396–402 (1965).

Nzeh and Adetoro, "Sonographic assessment of the incompetent cervix in pregnancy." Int. J. Gynecol. Obstet. 37:179–184 (1992).

Norwitz et al., "The Control of Labor." New Eng. J. of Med. 341(9):660–666 (1999).

Rush et al., "Contribution of preterm delivery to perinatal mortality." British Medical Journal 2:965–968 (1976).

Villar et al., "Pre–term delivery syndrome: the unmet need." Res. Clin. Forums 16(3):9–33 (1994).

* cited by examiner

DEVICES AND METHODS FOR CERVIX MEASUREMENT

BACKGROUND OF THE INVENTION

FIELD OF THE INVENTION

The present invention relates to medical devices and methods of using such devices. More particularly, the invention relates to instruments and methods to measure the length of the cervix in the fornix vaginae and the dilation of the cervix uteri.

BACKGROUND INFORMATION

Preterm labor, or labor before 37 weeks gestation, has been reported in 7 to 10 percent of all births but accounts for more than 85 percent of all perinatal complications and death. Rush et al., *BMJ* 2:965–8 (1976) and Villar et al., *Res. Clin. Forums* 16:9–33 (1994), which are both incorporated herein by reference. An inverse relationship between cervical length in the fornix vaginae and the risk of preterm labor has also been observed. Anderson et al., *Am. J. Obstet. Gynecol.* 163:859 (1990); Iams et al., *N. Eng. J. Med.* 334:567–72 (1996) and Heath et al., and *Ultrasound Obstet. Gynecol.* 12:312–7 (1998), which all are incorporated herein by reference. Accordingly, many physicians find it useful to examine the cervix in the fornix vaginae as part of normal prenatal care in order to assess risk of preterm labor.

It has long been known that the cervix normally undergoes a series of physical and biochemical changes during the course of pregnancy, which enhance the ease and safety of the birthing process for the mother and baby. For example, in the early stages of labor the tissues of the cervical canal soften and become more pliable, the cervix shortens (effaces), and the diameter of the proximal end of the cervical canal begins to increase at the internal os. As labor progresses, growth of the cervical diameter propagates to the distal end of the cervical canal, toward the external os. In the final stages of labor, the external os dilates allowing for the unobstructed passage of the fetus.

In addition to the physical and biochemical changes associated with normal labor, genetic or environmental factors, such as medical illness or infection, stress, malnutrition, chronic deprivation and certain chemicals or drugs can cause changes in the cervix. For example, it is well known that the in utero exposure of some women to diethylstilbestrol (DES) results in cervical abnormalities and in some cases gross anatomical changes, which leads to an incompetent cervix where the cervix matures, softens and painlessly dilates without apparent uterine contractions. An incompetent cervix can also occur where there is a history of cervical injury, as in a previous traumatic delivery, or as a result of induced abortion if the cervix is forcibly dilated to large diameters. Details of the incompetent cervix are discussed in Sonek, et al., *Preterm Birth, Causes, Prevention and Management*, Second Edition, McGraw-Hill, Inc., (1993), Chapter 5, which is incorporated by reference herein.

Cervical incompetence is a well recognized clinical problem. Several investigators have reported evidence of increased internal cervical os diameter as being consistent with cervical incompetence (see Brook et al., *J. Obstet. Gynecol.* 88:640 (1981); Michaels et al., *Am. J. Obstet. Gynecol.* 154:537 (1986); Sarti et al., *Radiology* 130:417 (1979); and Vaalamo et al., *Acta Obstet. Gynecol. Scan* 62:19 (1983), all of which are incorporated by reference herein). Internal os diameters ranging between 15 mm to 23 mm have been observed in connection with an incompetent cervix. Accordingly, a critical assessment in the diagnosis of an incompetent cervix involves measurement of the internal cervical os diameter.

There are also devices and methods to measure the diameter of the external cervical os. For example, cervical diameter can be manually estimated by a practitioner's use of his or her digits. Although an individual practitioner can achieve acceptable repeatability using this method, there is a significant variation between practitioners due to the subjective nature of the procedure. To address these concerns, various monitoring and measuring devices and methods have been developed. For example, an instrument for measuring dilation of the cervix uteri is described in U.S. Pat. No. 5,658,295. However, this device is somewhat large, leading to a risk of injury to the fundus of the vagina or cervical os. Additionally, it is not disposable and requires repeated sterilization. Another device for measuring cervical diameter is described, for example, in U.S. Pat. No. 6,039,701. In one version, the device described therein has a loop element which is secured to the cervix. The loop expands or contracts with the cervix and a gauge is coupled to the loop for measuring changes in the loop dimension. Such changes can then be detected by electronic means. Accordingly, this device is rather complex and expensive to manufacture.

Even if a woman is found to have an apparently normal internal cervical os diameter, there may nonetheless be a risk for preterm labor and delivery. Currently, risk assessment for preterm delivery remains difficult, particularly among women with no history of preterm birth. However, the findings that preterm delivery is more common among women with premature cervical shortening or effacement suggest that a measuring the length of the cervix would be predictive for preterm labor.

Currently, a physician has at least two options to measure the length of the cervix in the fornix vaginae. One such method involves serial digital examination of the cervix by estimating the length from the external cervical os to the cervical-uterine junction, as palpated through the vaginal fornix. Although this is useful for general qualitative analysis, it does not afford an easy nor accurate measurement of the length of the cervix from the external cervical os to the cervical-uterine junction (also described herein as the length of the cervix extending into the vagina) and, therefore, does not provide an accurate assessment of the risk of preterm labor. Despite the use of gloves, vaginal exams always carry with them the risk of transmitting infectious agents, especially to the fetal membranes, the lining and/or muscle of the uterus, or to the fetus itself Another method involves real-time sonographic evaluation of the cervix. This method provides relatively quick and accurate cervical dimensions. However, it requires expensive equipment, highly skilled operators, as well as skill in interpretation of results, which are all subject to human error. Additionally, there is a risk that the probe that must be inserted into the vagina as part of the procedure may cause injury if not inserted with care. Also, due to the expense of the procedure many women, especially those without proper health insurance, cannot afford to have a sonographic test performed.

It would be beneficial if there were an instrument a practitioner could use to measure the cervix quickly and accurately, and with little material expense. Although there are several instruments available for determining various dimensions of the uterus, there is no suitable instrument for measuring the length of the cervix in the fornix vaginae. For example, U.S. Pat. No, 4,016,867 describes a uterine caliper and depth gauge for taking a variety of uterine measurements, which although useful for fitting an intrauterine contraceptive device, is not capable of measuring the length of the cervix in the fornix vaginae due to interference by the caliper's wings. In fact, similar devices described in U.S. Pat. Nos. 4,224,951; 4,489,732; 4,685,474; and 5,658,295 suffer from similar problems due to their use of expandable wings or divergable probe tips. These devices are also relatively sophisticated, making them expensive to manufacture and purchase. U.S. Pat. No. 3,630,190 describes a flexible intrauterine probe, which is particularly adapted to measuring the distance between the cervical os and the fundus of the uterus. The stem portion of the device has a plurality of annular ridges spaced apart from each other by a predetermined distance, preferably not more than one-half inch apart. However, this device is not adapted for accurately measuring the length of the cervix in the fornix vaginae because of the lack of an appropriate measuring scale and a stop for automatically recording the measurement.

Accordingly, there is currently no commercially available, quick, inexpensive as well as accurate device to assess the risk of preterm labor by measuring the length of the cervix in the fornix vaginae. Therefore, many women at risk for preterm labor may be unaware of the risk to their pregnancy and their unborn child. If such a device were available, many more women would be better informed about the course of their pregnancy and would then be able to make better choices about becoming pregnant at all, or about managing their pregnancy to reduce the risk of preterm labor and injury to the unborn child.

Thus, there exists a need for a simple and inexpensive device that can be used to determine the length of the cervix in the fornix vaginae and, thus, predict the risk of preterm labor, as well as other conditions. There is also a need for such a device that can measure the dilation of the cervix uteri, to provide an overall assessment of the cervix and to determine the particular stage of labor. Ideally, the device should be adapted for use by a physician or obstetrician or even a trained nurse in the doctor's office or clinic. Preferably, the device should be sterile and disposable. In addition, it is desirable that device record the measurement automatically. The present invention satisfies these needs and provides related advantages as well.

SUMMARY OF THE INVENTION

The present invention provides a device for determining a dimension of a female reproductive organ. The device has an elongated member having a distal region and a proximal region, and a stop slidably engaged with the elongated member on the distal region. The stop has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip. Preferably, the dimension of the female reproductive organ is the length of the cervix in the fornix vaginae.

The invention also provides a device for determining the length of the cervix in the fornix vaginae. The device has an elongated member having a distal region and a proximal region, and a stop slidably engaged with the elongated member on the distal region. The stop has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip.

The invention further provides a device for determining a dimension of the fornix vaginae. The device has an elongated member having a distal region and a proximal region, and a stop slidably engaged with the elongated member on the distal region. The stop has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip.

The invention also provides a device for determining the depth of the uterus. The device has an elongated member having a distal region and a proximal region, a measuring scale on the distal region of the elongated member, and a stop slidably engaged with the elongated member on the distal region. The stop has a surface adapted to contact the cervix when the distal region of the elongated member is inserted into the vagina. Additional embodiments of the device are made of plastic, the distal region of the elongated member has an end formed for non-abrasive contact with a tissue, and the proximal region of the elongated member has a hand grip.

The invention further provides a device for measuring the dilation of cervix uteri. The device has an elongated member having a distal region, a proximal region and a bend in the elongated member at or near the distal region such that the distal region and the proximal region are approximately perpendicular to one another. The device also has a measuring scale on the distal region of the elongated member and a stop slidably engaged with the elongated member on the distal region. The stop has a surface adapted to contact the cervix when the distal region of the elongated member is inserted into the vagina. Additional embodiments of the device are made of plastic, the distal region of the elongated member has an end formed for non-abrasive contact with a tissue, and the proximal region of the elongated member has a hand grip.

The invention also provides methods using the devices disclosed herein. For example, the invention provides a method for predicting the risk of preterm labor in an individual by the steps of: inserting into the vagina a device comprising an elongated member having a distal region and a proximal region, and a stop slidably engaged with the elongated member on the distal region, and the stop has a surface adapted to contact the cervix when the distal region of the elongated member is inserted into the vagina; until the stop contacts the cervix and the distal region contacts the cervical-uterine junction at the fornix vaginae; and determining the length of the cervix in the fornix vaginae by observing the position of the stop along said elongated member, wherein the length of the cervix in the fornix vaginae is inversely related to the risk of preterm labor.

The invention also provides a method for predicting the risk of miscarriage in an individual by the steps of: inserting into the vagina a device having an elongated member having a distal region and a proximal region, and a stop slidably engaged with the elongated member on the distal region, and the stop has a surface adapted to contact the cervix when the distal region of the elongated member is inserted into the vagina, until the stop contacts the cervix and the distal region contacts the cervical-uterine junction at the fornix vaginae; and determining the length of the cervix in the fornix vaginae by observing the position of the stop along the elongated member, wherein the length of the cervix in the fornix vaginae is inversely related to the risk of miscarriage.

The invention also provides a method for predicting the ease of inducing labor in an individual by the steps of: inserting into the vagina a device having an elongated member having a distal region and a proximal region, and a stop slidably engaged with the elongated member on the distal region, and the stop has a surface adapted to contact the cervix when the distal region of the elongated member is inserted into the vagina, until the stop contacts the cervix and the distal region contacts the cervical-uterine junction at the fornix vaginae; and determining the length of the cervix in the fornix vaginae by observing the position of the stop along the elongated member, wherein the length of the cervix in the fornix vaginae is inversely related to the ease of inducing labor.

The invention further provides a method for assessing the fertility of an individual by the steps of: inserting into the vagina a device having an elongated member having a distal region and a proximal region, and a stop slidably engaged with the elongated member on the distal region, and the stop has a surface adapted to contact the cervix when the distal region of the elongated member is inserted into the vagina, until the stop contacts the cervix and the distal region contacts the cervical-uterine junction at the fornix vaginae; and determining the length of the cervix in the fornix vaginae by observing the position of the stop along the elongated member, wherein the length of the cervix in the fornix vaginae is inversely related to the fertility of an individual.

In addition, the invention provides methods for measuring the dilation of a cervix uteri, where the cervix uteri comprises one side and an opposite side, the method comprising, inserting into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a stop slidably engaged with the elongated member on the distal region, the stop having a surface adapted to contact one side of the cervix uteri when the distal region of the elongated member is inserted into the vagina, until the stop contacts one side of the cervix uteri at or near the external os; moving the device laterally such that the stop remains in contact with one side of the cervix uteri at or near the external os and such that the stop slides along the elongated member until an end of the elongated member at the distal region is in alignment with the opposite side of the cervix uteri at or near the external os; and determining the dilation of the cervix uteri by observing the position of the stop on the measuring scale on the elongated member.

DETAILED DESCRIPTION OF THE INVENTION

The present invention provides various devices and methods for determining dimensions of female reproductive organs. For example, the device is particularly adapted for determining the length of the cervix in the fornix vaginae, which, as described above, is related to the risk of preterm labor in an individual. The device is also suited for determining the dilation of the cervix uteri, for predicting the risk of preterm labor or the particular stage of delivery. However, it is contemplated herein, and also understood by those skilled in the art that the invention can be used not only for determining various dimensions of female reproductive organs, but for determining the dimension of any body cavity or passageway where such a device would be insertable, such as a vagina, uterus, mouth, throat, nasal cavity, ear channel, rectum, and also to any cavity created and opened by surgery, for example, during chest, abdominal or brain surgery. The device is also preferably fabricated from inexpensive materials and the measurement is quick to perform. Thus it allows the practitioner to repeat the test over time and therefore to more closely monitor a woman's pregnancy and risk for preterm labor. It is also contemplated that the device record the various measurements automatically, where the only input required by the practitioner is the proper insertion of the device into the body cavity or passageway. This is accomplished by the use of the stop.

Figure 1:
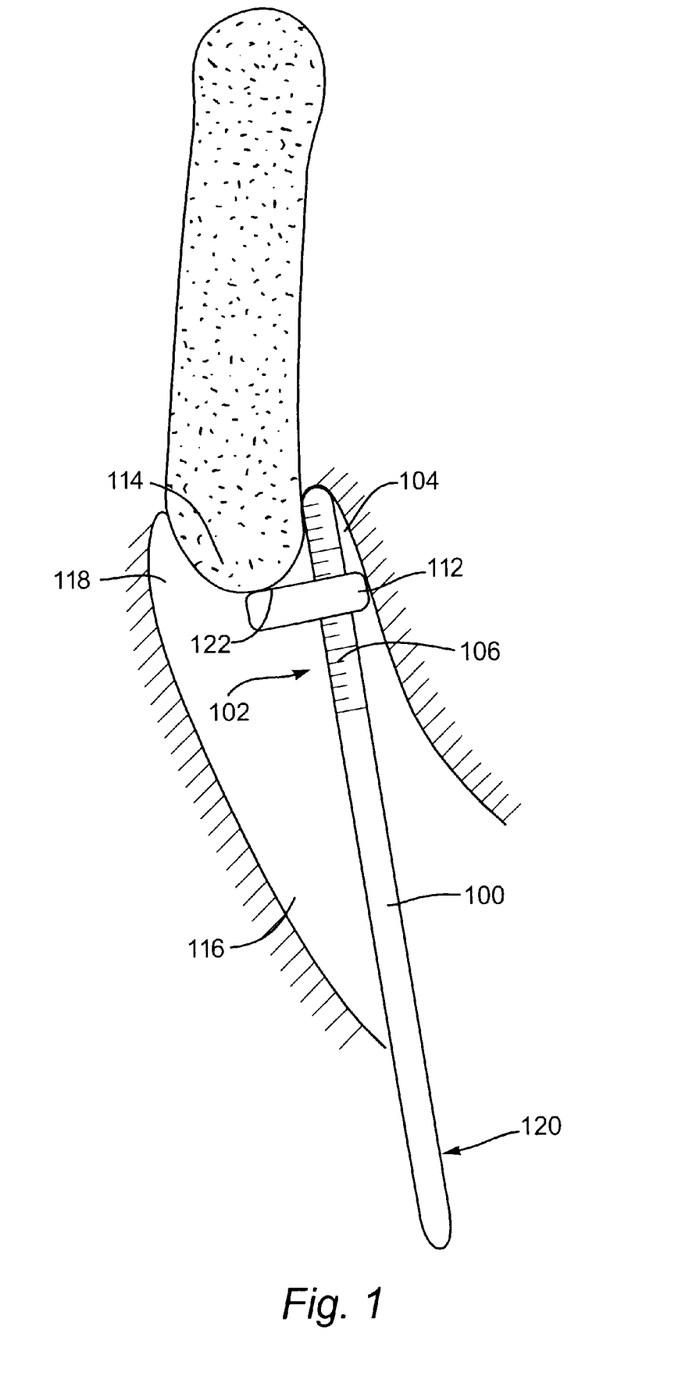
FIG. 1 shows a side view of the female reproductive system with placement of the device in the anterior fornix at the cervical-uterine junction with the stop contacting the cervix.

One dimension of a female reproductive organ that the device is adapted for, as shown in FIG. 1, for example, is measuring the length of the cervix 114 in the fornix vaginae 118. As used herein, the term "length of the cervix in the fornix vaginae" refers to and is used interchangeably with "the length of the cervical os to the cervical-uterine junction." Also used herein, the term "fornix vaginae" refers to the recess formed between the vaginal wall and the vaginal part of the cervix. The fornix vaginae may be divided into pars anterior (the anterior fornix), the pars posterior (posterior fornix) and the pars lateralis (lateral fornix), depending on its relation to the walls of the vagina. The device of the invention can be inserted into any of these parts of the fornix vaginae, depending on the choice of the user, to determine either the depth of the fornix vaginae at any particular point, or the length of the cervix in the fornix vaginae.

The device in FIG. 1 for determining a dimension of a female reproductive organ comprises an elongated member 100 having a distal region 102 and a proximal region 120, and a stop 112 slidably engaged with the elongated member 100 on the distal region 102, said stop 112 having a surface 122 adapted to contact the reproductive organ when the distal region 102 of the elongated member 100 is inserted thereinto. In order to properly use the device to measure the length of the cervix in the fornix vaginae, the stop must be initially at or near the distal end of the elongated member so as to be able to contact a body tissue when the distal end of the elongated member is inserted. If the stop is too far away from the distal end, such as for example at the proximal end, then the stop will not contact the tissue desired and no measurement will be recorded.

Figure 2:
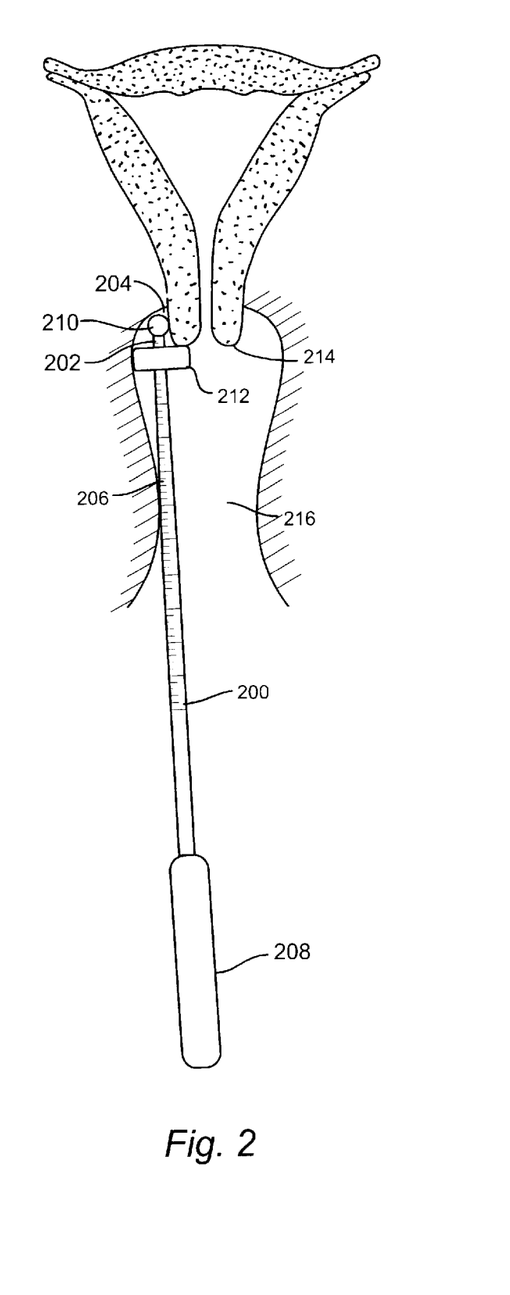
FIG. 2 shows alternative placement of the device in the lateral fornix at the cervical-uterine junction with the stop contacting the cervix.
Figure 4A:
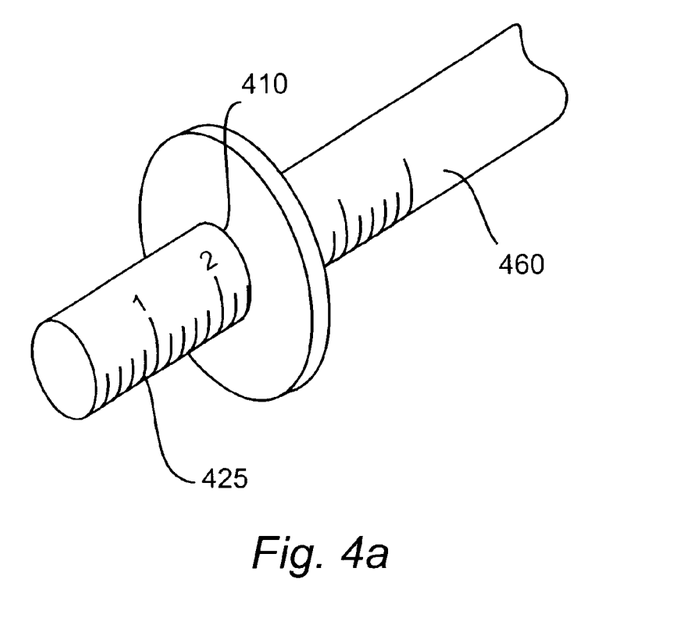
FIG. 4a shows an embodiment of the device with a round elongated member.
Figure 4B:
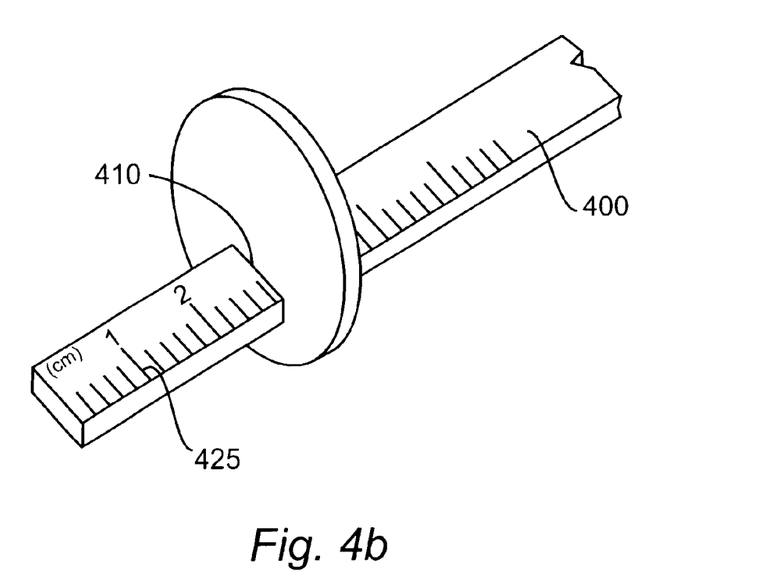
FIG. 4b shows an alternative embodiment of the device with a flat elongated member.

As used herein the "elongated member" comprises a rod, a stick or a strip, which may be flexible or rigid, rectilinear, annular, ovoid or other suitable shapes in cross-section and made from a biologically inert plastic material. One skilled in the art understands that various other cross-sectional shapes are contemplated as well. A round elongated member 410 is seen in FIG. 4a. A flat elongated member 420, which may be a strip, for example, is seen in FIG. 4b. Additionally, the elongated member may be tapered, with a narrower diameter on the distal region and a larger diameter on the proximal region, such that the stop is prevented from traveling too far down the elongated member in the direction of the proximal end. In any embodiment, preferably the elongated member will be sterile to reduce the risk of infection. Accordingly, the device should be commercially provided in a sealed package. Alternatively, the elongated member can be made from stainless steel if desired. However, the use of biologically inert plastic material or the like significantly reduces costs. Additionally, the elongated member may have an end on the distal region, the end shaped for non-abrasive contact with a tissue. As seen in FIG. 2, for example, this end 210 can comprise a spherical head or nodule or any other non-abrasive shape to reduce irritation and scraping of the cervical canal, fundus of the vagina or perforation of the fundus of the uterus.

As used herein the term "distal region" refers to a region of the elongated member which is adapted to be inserted first into the body cavity or passageway. As such, it will be that part of the device away from the hand of the user. As used herein the term "proximal region" refers to an area or region of the device near the user and can have, if desired, a hand grip.

As seen in FIG. 1, the practitioner can place the device so that the distal region 102 is in the anterior fornix 104. The elongated member 100 has a measuring scale 106, and if desired, although not required, a hand grip or handle on the proximal region 120 (not shown). Preferably, the distal region 102 has an end formed for non-abrasive contact with the tissue. A further example of such an end is a spherical head or nodule. The stop 112 contacts the end of the cervix 114 and slides along the elongated member 100 as the distal region 102 approaches the anterior fornix 104. The distance between the stop 112 and end 110 represents the length of the cervix in the vagina 116.

Alternatively, the practitioner can place the device in the lateral fornix 204, if desired, as shown in FIG. 2. The elongated member 200 preferably has a measuring scale 206, and if desired, although not required, a handle or hand grip 208. Preferably, the distal region 202 has an end 210 formed for non-abrasive contact with the tissue. The stop 212 contacts the end of the cervix 214 and slides along the elongated member 200 as the distal region 202 approaches the lateral fornix 204. The distance between the stop 212 and end 210 represents the length of the cervix in the vagina 216.

Preferred embodiments of the device have a measuring scale on the distal region of the elongated member. For example, in FIG. 4a and FIG. 4b, the measuring scale 425 is shown. As used herein, the "measuring scale" refers to any number of a series of visual markings on the elongated member at or near the distal end, which relate a measurement or distance. In a particular preferred embodiment, the measuring scale will provide 1 mm incremental markings along the length of the elongated rod, starting at the distal end such that the markings accurately reflect the length of the elongated member along any point thereof. For example, the first marking would be one millimeter from the end of the end of elongated member and would be marked with a single line indicating 1 mm.

Figure 5:
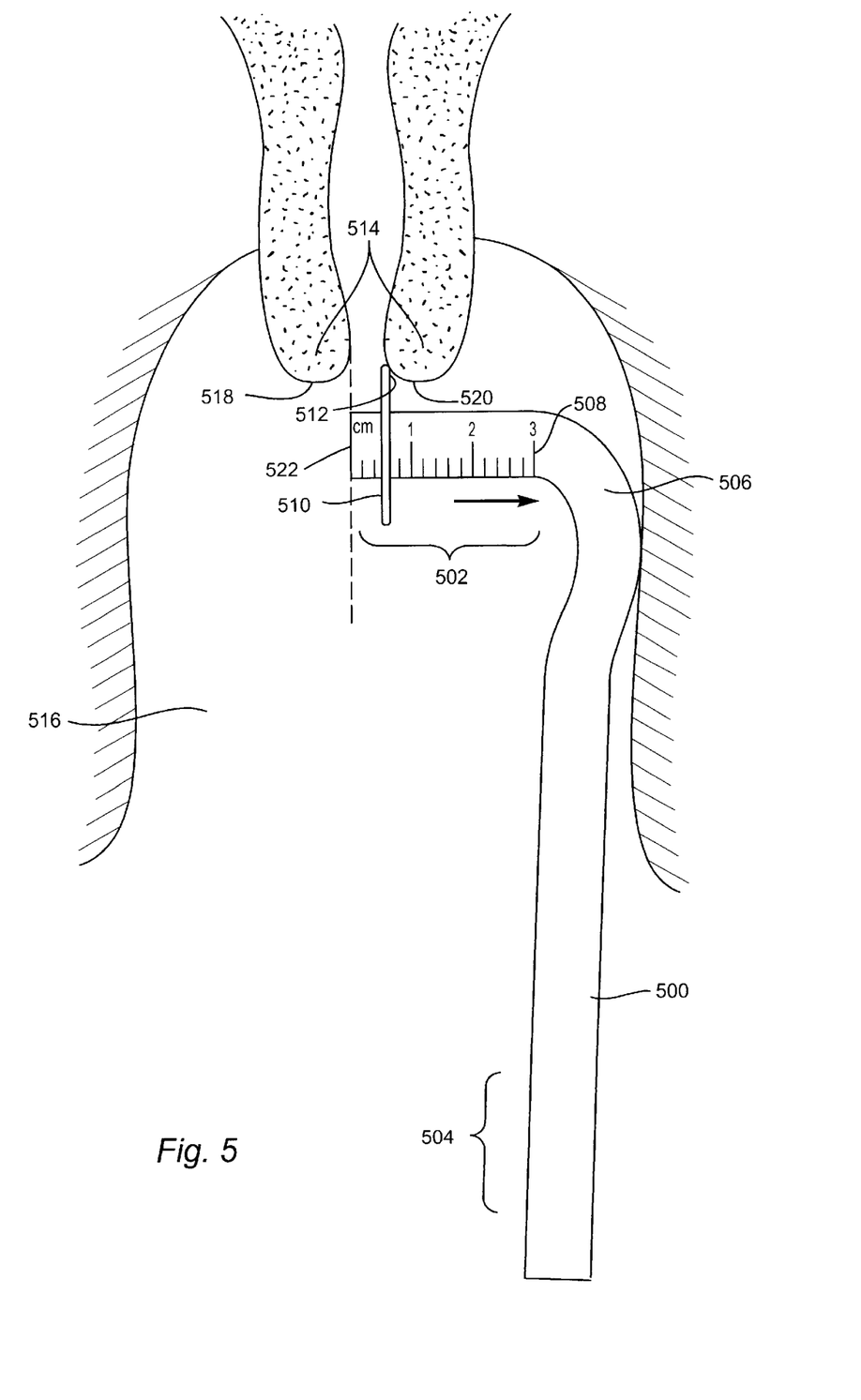
FIG. 5 shows an additional embodiment of the device for determining the dilation of the cervix uteri.

Another dimension of a female reproductive organ that the device is adapted for determining is the dilation of the cervix uteri during pregnancy, during various stages of labor, or even when the female is not pregnant. Traditionally, the dilation of the cervix uteri is used to predict when delivery is imminent. However, the dilation of the cervix uteri may provide an indication of whether a cervix is incompetent, which would be an important consideration to be aware of even before a female becomes pregnant. In this embodiment of the device, seen in FIG. 5, the device comprises an elongated member 500 having a distal region 502 and a proximal region 504, and a bend or turn 506 in the elongated member 500 at or near the distal region 502 such that the distal region 502 and the proximal region 504 are approximately perpendicular to one another. The device also preferably has a measuring scale 508 on the distal region 502 of the elongated member 500 and a stop 510 slidably engaged with the elongated member 500 on the distal region 502, the stop 510 having a surface 512 adapted to contact the cervix uteri 514 when the elongated member 500 is inserted into the vagina 516. Although the use of a bend in the elongated member is preferred, one skilled in the art understands that the elongated member may comprise any suitable shape which allows the dilation of the cervix uteri to be determined. For example, the elongated member may merely be flexible enough to allow the distal end to contact one side of the cervix uteri and the stop to contact the other side of the cervix uteri, thereby affording a measurement of the dilation of the cervix.

As used herein, the term "cervix uteri" refers to the neck of the uterus, or the lower and narrow end of the uterus between the isthmus and the ostium uteri. In the cross-sectional view of the cervix uteri 514 shown in FIG. 5 for example, the cervix uteri 514 comprises a left side 518 and a right (or opposite) side 520.

In this embodiment of the device, the stop 510 is initially placed away from the distal region 502 and near the bend 506. The distal region 502 of the elongated member 500 is inserted into the vagina until a surface of the stop 510 contacts the right side 520 of cervix uteri 514, for example. (If desired, the stop 510 can alternatively be placed into contact with the left side 518 of the cervix uteri 514.) The practitioner then moves the elongated member 500 laterally, in the direction of the arrow in FIG. 5, such that the stop 510 remains in contact with the right side 520 and also such that the stop 510 slides along the measuring scale 508. When the end 522 of the distal region 502 is lined up with the left side 518 of the cervix uteri 514, (shown by a dashed line in FIG. 5), the position of the stop 510 is observed and the measurement of the dilation of the cervix uteri 514 is obtained.

Figure 3:
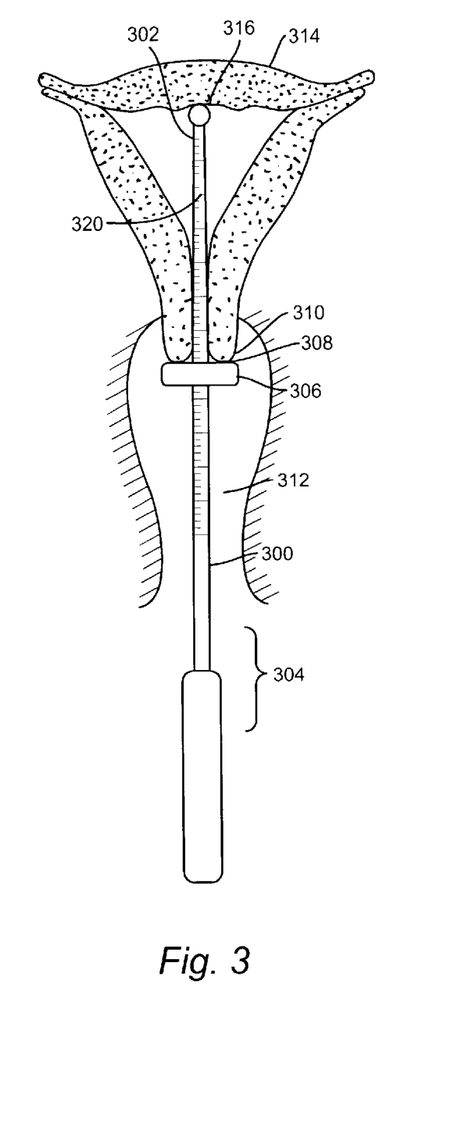
FIG. 3 shows placement of the device to determine the depth of the uterus.

Additionally, the device may be adapted for determining the depth of the uterus as seen in FIG. 3, which is particularly useful, for example, in fitting an intrauterine contraceptive device, where a measurement of the inner dimensions of the uterus are desired. In this embodiment, the device comprises an elongated member 300 having a distal region 302 and a proximal region 304, and a stop 306 slidably engaged with the elongated member 300 on the distal region 302, the stop 306 having a surface 308 adapted to contact the cervix 310 when the elongated member 300 is inserted into the vagina 312. As seen in FIG. 3, the distal region 302 of the elongated member 300 is inserted into the uterus 314 until resistance caused by contact of the end of the elongated member 300 on the fundus 316 of the uterus 314 is felt by the user. During the insertion the stop 306 has already contacted the opening of the cervix 310 and resistance from the cervix 310 causes the stop 306 to slide along the elongated member 300 as the elongated member 300 is inserted farther into the uterus 314. Accordingly, when the user removes the device, the position of the stop 306 along the measuring scale 320 provides an accurate measurement of the depth of the uterus 314.

As used herein, the term "depth of the uterus" refers to the distance between the end of the cervix in the vagina and the fundus of the uterus at a point farthest above the cervical canal. A practitioner would desire to determine the depth of the uterus for fabrication of an intrauterine contraceptive device, for example.

As used herein the term "slidably engaged" refers to the particular form of attachment of the stop to the elongated member. Any form of attachment is contemplated provided that the stop is allowed to move along the elongated member with less resistance than would otherwise cause deformation of the cervix or any body cavity that it contacts, and while at the same time ensuring that the stop does not become disengaged, or fall off of the elongated member. As shown in FIGS. 4a and 4b, a hole 410 is formed in the stop, the hole being sized to slidably engage or fit along the elongated member. In FIG. 4a, the hole 410 is round, since the elongated member 400 is round or annular in cross-section. In FIG. 4b, the hole 410 is rectilinear, since the elongated member 400 is rectilinear.

Preferably, the stop will be a rounded shape suitably large enough for contacting the end of the cervix in the vaginal space, without being too large to fit into the vagina or into the fornix vaginae. However, one skilled in the art understands that the stop may be any other suitable shape, such as rectilinear, square or the like. A rounded shape is preferred in order to minimize injury to the surrounding tissues. Also preferably, the stop will be larger than the external cervical os, thereby preventing it from entering the cervical canal. One skilled in the art understands that any other shape or size of the stop may be used instead, for example a bar or a rod, so long as it is able to contact the cervix or other body tissue. Also in a preferred embodiment, the stop will be made from a biologically inert plastic material, like the elongated member.

The present invention also provides various methods using the devices. For example, the invention provides a method for predicting the risk of preterm labor in an individual by the steps of: inserting into the vagina a device comprising an elongated member having a distal region and a proximal region, and a stop slidably engaged with the elongated member on the distal region, and the stop has a surface adapted to contact the cervix when the distal region of the elongated member is inserted into the vagina; until the stop contacts the cervix and the distal region contacts the cervical-uterine junction at the fornix vaginae; and determining the length of the cervix in the fornix vaginae by observing the position of the stop along said elongated member, wherein the length of the cervix in the fornix vaginae is inversely related to the risk of preterm labor.

As used herein the term "risk of preterm labor" refers to the risk that an individual will enter labor before the thirty-seventh week of gestation or pregnancy. Using the methods and devices of the present invention, this risk can be predicted either when the individual is already pregnant or when the individual is not pregnant. As such this can give the woman valuable insight on that may occur during the pregnancy. Also as used herein the term "preterm delivery" is used interchangeably with preterm birth and refers to birth of the fetus as the result of preterm labor. Accordingly, it is contemplated that preterm delivery would occur as the result of preterm labor. Because babies born prematurely may have serious health problems, practitioners try to avoid preterm labor if at all possible. If vaginal bleeding occurs or if the fetal membranes rupture, preterm labor is difficult to stop. However, if vaginal bleeding does not occur, and the membranes are not leaking amniotic fluid, bed rest with fluid given intravenously helps approximately one in two women. However, if the cervix dilates beyond 5 centimeters, labor usually continues until the baby is born. Typically, magnesium sulfate given intravenously stops labor in a majority of cases. Using the devices and methods of the present invention will indicate whether such treatment may be needed in the future.

The invention also provides a method for predicting the risk of miscarriage in an individual inserting into the vagina a device having an elongated member having a distal region and a proximal region, and a stop slidably engaged with the elongated member on the distal region, and the stop has a surface adapted to contact the cervix when the distal region of the elongated member is inserted into the vagina, until the stop contacts the cervix and the distal region contacts the cervical-uterine junction at the fornix vaginae; and determining the length of the cervix in the fornix vaginae by observing the position of the stop along the elongated member, wherein the length of the cervix in the fornix vaginae is inversely related to the risk of miscarriage.

The present invention also provides methods for predicting the ease of inducing labor by inserting into the vagina a device comprising, an elongated member having a distal region and a proximal region; and a stop slidably engaged with the elongated member on the distal region, the stop having a surface adapted to contact the cervix when the elongated member is inserted into the vagina, until the stop contacts the cervix and the distal region contacts the cervical-uterine junction at the fornix vaginae; and determining the length of the cervix in the fornix by observing the position of the stop along the elongated member, wherein the length of the cervix in the fornix vaginae is inversely related to the ease of inducing labor.

The invention further provides a method for assessing the fertility of an individual by inserting into the vagina a device having an elongated member having a distal region and a proximal region, and a stop slidably engaged with the elongated member on the distal region, and the stop has a surface adapted to contact the cervix when the distal region of the elongated member is inserted into the vagina, until the stop contacts the cervix and the distal region contacts the cervical-uterine junction at the fornix vaginae; and determining the length of the cervix in the fornix vaginae by observing the position of the stop along the elongated member, wherein the length of the cervix in the fornix vaginae is inversely related to the fertility of an individual.

As used herein, the term "fertility" refers to the ability of a female to carry a fetus to the point where it is viable, or can survive with the help of medical science, if necessary, when delivered. Accordingly, fertility refers to the ability of a female to carry a fetus to a normal nine month term, as well as to any other shorter term where the infant would survive on its own or with critical care. By assessing the cervical length and diameter, a practitioner achieves an appreciation of the fertility of the female, because a risk for preterm labor can be predicted. For example, the practitioner can determine that a female is at such a risk for preterm labor and preterm delivery that the chances of survival of the infant would be small, then the practitioner can advise the female of the risk. Accordingly, the female can make the decision to avoid pregnancy or can, with the assistance of her physician, take steps through diet, rest, and medications to lessen the risk of preterm labor.

As used herein the term "female" refers to a mammalian female, such as a human, horse, dog, cow, pig or monkey. Although the devices and methods are particularly adapted for use in a human female, one skilled in the art understands that they may be used in any female mammal. Accordingly, the devices and methods of the present invention could be used in veterinary medicine, if desired.

In addition, the invention provides methods for measuring the dilation of a cervix uteri, where the cervix uteri comprises one side and an opposite side, the method comprising, inserting into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a stop slidably engaged with the elongated member on the distal region, the stop having a surface adapted to contact one side of the cervix uteri when the distal region of the elongated member is inserted into the vagina, until the stop contacts one side of the cervix uteri at or near the external os; moving the device laterally such that the stop remains in contact with one side of the cervix uteri at or near the external os and such that the stop slides along the elongated member until an end of the elongated member at the distal region is in alignment with the opposite side of the cervix uteri at or near the external os; and determining the dilation of the cervix uteri by observing the position of the stop on the measuring scale on the elongated member.

EXAMPLE I

Cervix Length Measurement

This example provides measurement of the length of the cervix in the vagina in a subject and correlation with reported criteria for determining the risk of preterm delivery.

The subject preferably lies in a prone position on her back. The practitioner uses a speculum to first examine the vaginal cavity and to observe the optimum position for placing the device. The practitioner inserts into the vagina a device comprising an elongated member having a distal region and a proximal region and a stop slidably engaged with the elongated member on the distal region, said stop having a surface adapted to contact the cervix when the distal region of the elongated member is inserted into the vagina. The device is inserted until the stop contacts the cervix and the distal region contacts the cervical-uterine junction at the fornix vaginae. Then the length of the cervix in the fornix vaginae is determined by observing the position of the stop on the elongated member. Since the length of the cervix in the fornix vaginae is inversely related to the risk of preterm delivery, such a risk can be determined. The practitioner uses the data provided herein in Table 1, which is discussed in Iams et al., *N. Eng. J. Med.* 334:567 (1996), which is also incorporated by reference herein, in order to determine the relative risk of preterm delivery.

TABLE I

| Length of cervix (mm) | Relative Risk of Preterm Delivery | | |
|---|---|---|---|
| | Percentile | at 24 weeks | at 28 weeks |
| 40 | ≦75 | 2 | 2.8 |
| 35 | ≦50 | 2.4 | 3.5 |
| 30 | ≦25 | 3.8 | 5.4 |
| 26 | ≦10 | 6.2 | 9.6 |
| 22 | ≦5 | 9.5 | 13.9 |
| 13 | ≦1 | 14 | 24.9 |

As used herein, the term "relative risk" refers to the likelihood that there will be a preterm delivery when compared to the population which does not have that finding. In this subject, the length of the cervix is determined to be 22 mm. Since the subject is at 24 weeks of gestation, the relative risk for preterm delivery for this subject is 9.5. In other words, this subject has a 9.5 higher risk for preterm delivery than an individual whose cervix is greater than 22 mm in length.

EXAMPLE II

Cervix Dilation Measurement

This example demonstrates the use of the invention disclosed herein to measure the dilation of the cervix uteri in the same subject as in Example 1, to predict the risk for preterm delivery or the particular stage of delivery in a normal pregnancy.

Using a device of the present invention to measure the dilation of the cervix uteri, the practitioner inserts into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a stop slidably engaged with the elongated member on the distal region, the stop having a surface adapted to contact one side of the cervix uteri when the distal region of the elongated member is inserted into the vagina, until the stop contacts one side of the cervix uteri at or near the external os. The practitioner then moves the device laterally such that the stop remains in contact with one side of the cervix uteri at or near the external os and such that the stop slides along the elongated member until an end of the elongated member at the distal region is in alignment with the opposite side of the cervix uteri at or near the external os. The practitioner determines the dilation of the cervix uteri by observing the position of the stop on the measuring scale on the elongated member. Using this procedure, the dilation of the cervix uteri in this subject is found to be 5 mm. Accordingly, the physician advises the subject that delivery is imminent. Since this subject is in her $24^{th}$ week of pregnancy, this delivery is premature or preterm.

Although the invention has been described with reference to the examples provided above, it should be understood that various modifications can be made without departing from the spirit of the invention. Accordingly, the invention is limited only by the claims.

I claim:

1. A device for determining length of the cervix in the fornix vaginae comprising:

a. an elongated member having a distal region and a proximal region;

b. a measuring scale disposed on the distal region of the elongated member; and c. a stop having a main body adapted to contact the cervix and an opening configured for slidable insertion of the distal region of the elongated member, wherein the main body is offset from said elongated member when the member is inserted into the opening.

2. The device of claim 1, wherein the stop lies substantially over the measuring scale when the elongated member is inserted into the opening of the stop.

3. The device of claim 1, wherein said elongated member comprises plastic.

4. The device of claim 1, wherein the distal region of said elongated member further comprises an end formed for non-abrasive contact with a tissue.

5. The device of claim 1, wherein the proximal region of said elongated member further comprises a hand grip.

6. A device for determining a dimension of the fornix vaginae comprising:

a. an elongated member having a cylindrical body, a distal region, and a proximal region;

b. a measuring scale on the distal region of said elongated member; and c. a stop having a body adapted to contact the cervix, and an opening configured for slidable insertion of the distal region of the elongated member, wherein the stop lies substantially over the measuring scale and the body is offset from the elongated member when the member is inserted through the opening.

7. The device of claim 6, wherein said elongated member comprises plastic.

8. The device of claim 6, wherein the distal region of said elongated member further comprises an end formed for non-abrasive contact with a tissue.

9. The device of claim 6, wherein the proximal region of said elongated member further comprises a hand grip.

10. A device for measuring dilation of cervix uteri comprising, a. an elongated member having a distal region, a proximal region, and a bend in said elongated member at or near said distal region such that said distal region and said proximal region are approximately perpendicular to one another;

b. a measuring scale on the distal region of said elongated member; and c. a stop slidably engaged with said elongated member on the distal region, said stop having a surface adapted to contact the cervix when the distal region of said elongated member is inserted into the vagina.

11. The device of claim 10, wherein said elongated member comprises plastic.

12. The device of claim 10, wherein the distal region of said elongated member further comprises an end formed for non-abrasive contact with a tissue.

13. The device of claim 10, wherein the proximal region of said elongated member further comprises a hand grip.

14. A method for measuring the dilation of a cervix uteri, where said cervix uteri comprises one side and an opposite side, said method comprising, a. inserting into the vagina a device comprising,
   i. an elongated member having a distal region, a proximal region, and a bend in said elongated member at or near said distal region such that said distal region and said proximal region are approximately perpendicular to one another;
   ii. a measuring scale on the distal region of said elongated member; and
   iii. a stop slidably engaged with said elongated member on the distal region, said stop having a surface adapted to contact one side of the cervix uteri when the distal region of said elongated member is inserted into the vagina, until the stop contacts one side of the cervix uteri at or near the external os;

b. moving the device laterally such that the stop remains in contact with said one side of the cervix uteri at or near the external os and such that the stop slides along the elongated member until an end of the elongated member at the distal region is in alignment with said opposite side of the cervix uteri at or near the external os; and c. determining the dilation of the cervix uteri by observing the position of the stop on the measuring scale on the elongated member.

15. The method of claim 14, wherein said elongated member comprises plastic.

16. The method of claim 14, wherein the end of said elongated member at the distal region further is formed for non-abrasive contact with a tissue.

17. The method of claim 14, wherein the proximal region of said elongated member further comprises a hand grip.

\* \* \* \* \*